United States Patent [19]

Sirrenberg et al.

[11] Patent Number: 4,782,091
[45] Date of Patent: Nov. 1, 1988

[54] BENZOYL(THIO)UREA ARTHROPODICIDES

[75] Inventors: Wilhelm Sirrenberg, Sprockhoevel; Benedikt Becker, Mettmann; Wolfgang Behrenz, Overath; Ingomar Krehen, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 118,906

[22] Filed: Nov. 10, 1987

[30] Foreign Application Priority Data

Nov. 25, 1986 [DE] Fed. Rep. of Germany ....... 3640175

[51] Int. Cl.⁴ .................... A01N 47/28; A01N 47/30; C07C 127/22
[52] U.S. Cl. .................... 514/594; 514/584; 564/23; 564/44
[58] Field of Search .................... 564/44, 23; 514/584, 514/594

[56] References Cited

U.S. PATENT DOCUMENTS

| Re. 30,563 | 3/1981 | Abdulla et al. | 564/44 |
|---|---|---|---|
| 4,457,943 | 7/1984 | Becher et al. | 564/44 |
| 4,533,676 | 8/1985 | Sirrenberg et al. | 564/44 |
| 4,711,905 | 12/1987 | Sirrenberg et al. | 564/44 |

*Primary Examiner*—Alan Siegel
*Attorney, Agent, or Firm*—Sprung, Horn, Kramer & Woods

[57] ABSTRACT

Arthropodicidally active novel benzoyl(thio)ureas of the formula

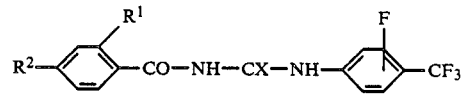

in which
X is oxygen or sulphur,
$R^1$ is halogen and
$R^2$ is halogen.

8 Claims, No Drawings

BENZOYL(THIO)UREA ARTHROPODICIDES

The present invention relates to new benzoyl(thio)ureas, several processes for the preparation thereof, and the use thereof as pesticides, in particular as arthropodicides and particularly preferably as insecticides.

It has already been disclosed that certain benzoylureas, such as, for example, 1-(3-chloro-4-trifluoromethylphenyl)-3-(2-chloro-4-fluorobenzoyl)-urea, have insecticidal properties (cf., for example, EP-A No. 93,976).

The new substituted benzoyl(thio)ureas of the general formula (I)

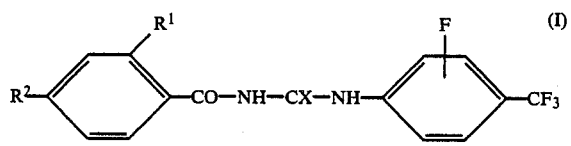

in which
X represents oxygen or sulphur,
R¹ represents halogen and
R² represents halogen,
have been found.

These new compounds have strong biological properties, in particular arthropodicidal and particularly preferably insecticidal properties, which make possible their use as pesticides, in particular as insecticides.

It has furthermore been found that the new substituted benzoyl(thio)ureas of the general formula (I) are obtained in a process in which (a) substituted anilines of the general formula (II)

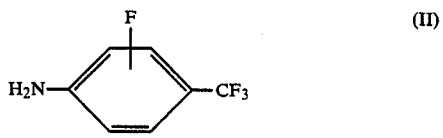

are reacted with benzoyl iso(thio)cyanates of the general formula (III)

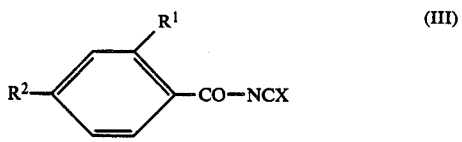

in which
X, R¹ and R² have the abovementioned meanings, if appropriate in the presence of a diluent, or (b) substituted phenyl iso(thio)cyanates of the general formula (IV)

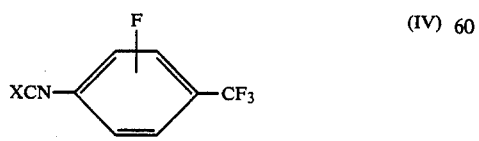

in which
X has the abovementioned meaning, are reacted with benzamides of the general formula (V)

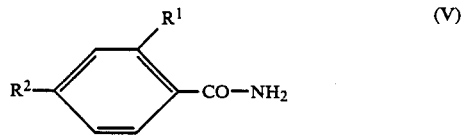

in which
R¹ and R² have the abovementioned meanings, if appropriate in the presence of a catalyst and if appropriate in the presence of a diluent.

In the definition of R¹ and R², halogen denotes fluorine, chlorine, bromine and iodine, preferably fluorine, chlorine and bromine, in particular fluorine and chlorine.

The new compounds of the general formula (I) have properties which make possible their use as pesticides, in particular they are distinguished both by an excellent and a long-term arthropodicidal activity, preferably an insecticidal activity.

The invention preferably relates to new compounds of the general formula (I), in which
X represents oxygen or sulphur (preferably oxygen),
R¹ represents fluorine, chlorine or bromine and
R² represents fluorine, chlorine or bromine.

Particularly preferred compounds of the general formula (I) are those in which
X represents oxygen or sulphur (preferably oxygen),
R¹ represents fluorine or chlorine, and
R² represents fluorine or chlorine.

Compounds of the general formula (I) in which
X represents sulphur,
R¹ represents fluorine or chlorine (preferably chlorine), and
R² represents fluorine or chlorine (preferably fluorine),
have a particularly good activity.

Furthermore, preferred compounds of the general formula (I) are those in which
X represents oxygen,
R¹ represents fluorine or chlorine (preferably chlorine) and
R² represents fluorine or chlorine (preferably fluorine).

Very particularly preferred compounds of the general formula (I) are those in which
X represents oxygen,
R¹ represents chlorine and
R² represents fluorine.

The fluorine atom in the phenyl part is in the 2- or 3-position, preferably in the 3-position (to the amino group).

If 2-chloro-4-fluorobenzoyl isothiocyanate and 3-fluoro-4-trifluoromethylaniline are used as starting materials according to the process variant (a), the course of the reaction may be represented by the following equation:

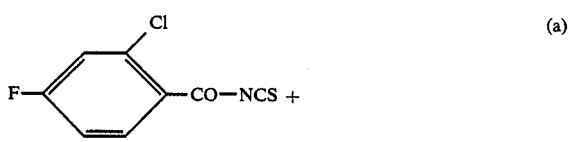

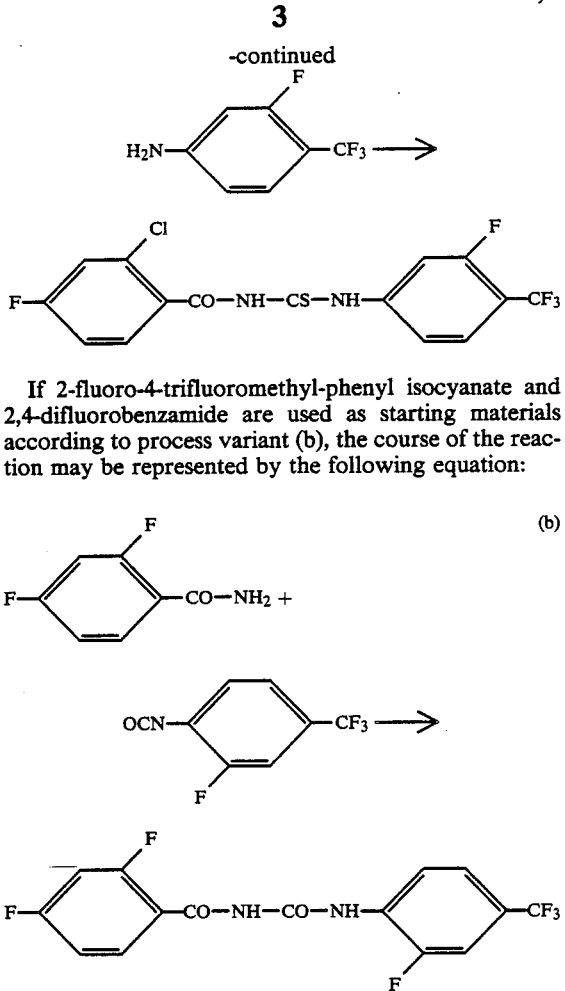

If 2-fluoro-4-trifluoromethyl-phenyl isocyanate and 2,4-difluorobenzamide are used as starting materials according to process variant (b), the course of the reaction may be represented by the following equation:

The starting compounds of the formula (II) are known or can be obtained by generally known methods.

The following may be mentioned as examples of compounds of the formula (II): 2-fluoro- and 3-fluoro-4-trifluoromethyl-aniline.

The starting compounds of the general formula (III) are known or can be obtained by generally known methods.

The following may be mentioned as examples of compounds of the formula (III): 2-chloro-4-fluoro-, 2,4-difluoro- and 2,4-dichloro-benzoyl isocyanate and isothiocyanate.

The starting compounds of the general formula (IV) are known, or the amino group of the compounds of the formula (II) can be converted into the isocyanate or isothiocyanate group by conventional processes, for example by reacting with phosgene or thiophosgene in diluents such as, for example, toluene and/or pyridine, at a temperature between −20° C. to +50° C.

The following may be mentioned as examples of compounds of the formula (IV): 2-fluoro- and 3-fluoro-4-trifluoromethyl-phenyl isocyanate and -phenyl isothiocyanate.

The starting compounds of the general formula (V) are likewise known or can be obtained by generally known methods.

The following may be mentioned as examples of compounds of the formula (V): 2-chloro-4 -fluoro-, 2,4 -difluoro- and 2,4-dichloro-benzamide.

Suitable diluents for carrying out process variants (a) and (b) are virtually all inert organic solvents. These include, in particular, aliphatic and aromatic, optionally halogenated hydrocarbons, such as pentane, hexane, heptane, cyclohexane, petroleum either, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl, methyl isopropyl and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and tetramethylene sulphone.

Catalysts which can be used for the reaction according to process variant (b) are preferably tertiary amines, such as triethylamine and 1,4-diazabicyclo[2,2,2]-octane, and also organotin compounds, such as, for example, dibutyltin dilaurate. However, the addition of such catalysts is not absolutely necessary.

The reaction temperature can be varied within a relatively wide range in process variants (a) and (b). In general, process variant (a) is carried out between 20° C. and 180° C., preferably between 40° C. and 120° C., and process variant (b) is carried out between 20° C. and 200° C., preferably between 60° C. and 190° C. The process variants according to the invention are generally carried out at atmospheric pressure.

The starting materials are usually employed in approximately equimolar amounts for carrying out the process variants according to the invention. An excess of one or the other reaction component brings no significant advantages.

The reaction products are worked up by conventional methods, for example by filtering off the precipitated product under suction or dissolving undesired byproducts out of the reaction mixture. The melting point is used for characterization.

The active compounds of the general formula (I) are suitable for combating animal pests, preferably arthropods, in particular insects, encountered in agriculture, in horticulture, in forestry, in the protection of stored products and of materials, and in the hygiene field, and have good plant tolerence and favorable toxicity to warm-blooded animals. They are active against normally sensitive and resistant species and against all or some stages of development. The above-mentioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, Scutigerella immaculata. From the order of the Thysanura, for example, *Lepisma saccharina.* From the order of Collembola, for example, Onychiurus armatus. From the order of Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Heamatopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus* spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophera gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and Tortrix viridana. From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomes spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenes spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstritialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xeropsylla cheopis* and Ceratophyllus spp. From the order of the Arachnida, for example, *Scorpio maurus* and *Latrodectus mactans.*

The active compounds, according to the invention, of the formula (I) are distinguished, in particular, by an excellent insecticidal activity. When used as insecticides, they exhibit an excellent action and a particularly long activity, preferably against beetle larvae, such as, for example, *Phaedon cochleariae,* and caterpillars (in particular of butterflies) such as, for example, *Spodoptera frugiperda.* In addition, the new compounds exhibit an excellent action in combating pests or hygiene pests, such as mosquito larvae and fly grubs, such as Musca (in particular *Musca domestica*) or Aedes (in particular *Aedes aegypti*).

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, perferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compounds of the formula (I) according to the invention are also suitable for combating arthropods which can occur in connection with agricultural productive livestock such as, for example, cattle, sheep, goats, horses, pigs, donkeys, camels, buffalo, rabbits, chickens, turkeys, ducks, geese, other pets, such as, for example, dogs, cats, cage birds and aquarium fish, and also so-called test animals, such as, for example, hamsters, guinea pigs, rats and mice. By combating these arthropods, cases of death and reductions in productivity (for meat, milk, wool, hides, eggs etc.) should be diminished, so that more economic and simpler animal husbandry is possible by using the active compounds according to the invention.

The active compounds according to the invention are administered in these areas by conventional methods (as are known from benzoylureas), for example by surface application in the form, for example, of dipping, spraying, pouring-on, spotting-on, washing, dusting and with the aid of molded articles containing the active compounds, such as collars, ear tags, tail tags, leg rings, halters, marking devices etc.

The activity of the compounds of the general formula (I) according to the invention will be described with reference to the following biological examples:

EXAMPLE A

Phaedon larvae test

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the specified periods of time, the destruction in % is determined. 100% means that all the beetle larvae have been killed; 0% means that none of the beetle larvae have been killed.

In this test the compound of preparation Example (2), for example, exhibited a destruction of 100% after 10 days at an active compound concentration of 0.0001%.

EXAMPLE B

Spodoptera test

Solvent: 15 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*), as long as the leaves are still moist.

After the desired periods of time, the destruction in % is determined. 100% means that all of the caterpillars have been killed; 0% means that none of the caterpillars have been killed.

In this test the compounds of preparation Examples (1) and (2), for example, exhibited a destruction of 100% after 7 days at an active compound concentration of 0.00001%.

EXAMPLE C

Mosquito larvae test

Test insects: *Aedes aegypti* at the 2nd larval stage
Solvent: 99 parts by weight of acetone
Emulsifier: 1 part by weight of benzyl hydroxydiphenyl polyglycol ether To produce a suitable preparation of active compound, 2 parts by weight of active compound are dissolved in 1,000 parts by volume of solvent containing the amount of emulsifier stated above. The solution thus obtained is diluted with water to the desired lower concentrations.

The aqueous preparations of active compound of the desired concentration are transferred into plastic beakers, and 20 mosquito larvae are subsequently placed in each beaker. The larvae are fed daily with fish feed (Tetramin ®).

The destruction in % is determined after 1 day, 8 days and 21 days. 100% here denotes that all larvae have been killed. 0% denotes that no larvae at all have been killed.

In this test, the compound of preparation Example (2), for example, exhibited a destruction of 100% after 8 days at an active compound concentration of $10^{-3}$ ppm.

EXAMPLE D $LD_{100}$ test
Test insects:
  *Musca domestica* (resistant) grubs
Number of test insects: 25
Solvent: acetone 2 parts by weight of active compound are taken up in 1,000 parts by volume of solvent. The solution thus obtained is diluted with further solvent to the desired concentration.

2.5 ml of the active compound solution are pipetted into a Petri dish. A filter paper disc of about 9.5 cm diameter is located on the bottom of the Petri dish. The Petri dish is left standing open until the solvent has completely evaporated. The amount of active compound per m² of filter paper varies, depending on the concentration of the active compound solution. The stated number of test insects is then introduced into the Petri dish, and the dish is covered with a glass lid.

The number of flies emerged is tested 14 days after starting the experiments and the degree of action according to Abbott determined in %. Here, 0% denotes that all the test insects have emerged and 100% denotes that no test insects have emerged.

In this test, the compounds of preparation xamples (1) and (4), for example, exhibited a prevention of emergence of 100% at an active compound concentration of 0.002%.

EXAMPLE E

Test with *Lucilia cuprina* resistant larvae
Emulsifier:
35 parts by weight of ethylene glycol monomethyl ether
35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. Larvae are introduced into a test tube which contains approx. 1 cm³ of horse meat and 0.5 ml of the preparation of active compound. After 24 hours, the degree of destruction is determined.

In this test, the compound of preparation Example (2), for example, exhibited a destruction of 100% at an active compound concentration of 100 ppm.

The preparation of the compound according to the invention is intended to be described by the following preparation examples.

EXAMPLE 1

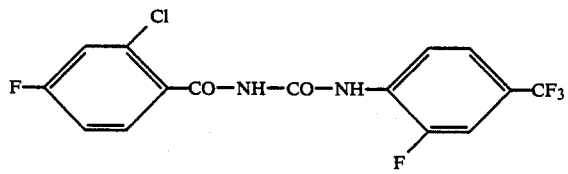

(Process variant (a))

A solution of 2.0 g (0.01 mol) of 2-chloro-4-fluorobenzoyl isocyanate in 100 ml of dry toluene is added to a solution of 1.79 g (0.01 mol) of 2-fluoro-4-trifluoromethylaniline in 40 ml of dry toluene, and the mixture is stirred for half an hour at 80° C. and subsequently concentrated in vacuo. The residue is washed with a little toluene and petroleum ether and subsequently dried.

3.4 g (90% of theory) of 1-(2-chloro-4-fluorobenzoyl)-3-(2-fluoro-4-trifluoromethyl-phenyl)-urea of melting point 194° C. are obtained.

EXAMPLE 2

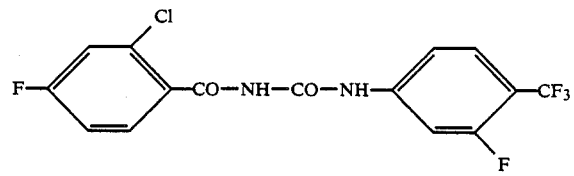

(Process variant (b))

A solution of 2.05 g (0.01 mol) of 3-fluoro-4-trifluoromethyl-phenyl isocyanate in 10 ml of dry toluene is added to a solution of 1.74 g (0.01 mol) of 2-chloro-4-fluorobenzamide in 40 ml of dry toluene at 60° C., and the mixture is refluxed for 7 hours. The reaction mixture is subsequently concentrated in vacuo. The residue is stirred with a little cold diethyl ether, separated off and dried.

3.2 g (84.5% of theory) of 1-(2-chloro-4-fluorobenzoyl)-3-(3-fluoro-4-trifluoromethyl-phenyl)-urea of melting point 181° C. are obtained.

The compounds of the formula (I) are shown in Table 1 below can be prepared analogously to Example 1 and 2 and process variant (a) or (b):

TABLE 1

$$R^2 \underset{}{\overset{R^1}{\bigcirc}} -CO-NH-CX-NH- \underset{CF_3}{\overset{F}{\bigcirc}} \quad (I)$$

| Example No. | R¹ | R² | X | | Melting point [°C.] |
|---|---|---|---|---|---|
| 3 | F | F | O | ![F-CF3 phenyl] | 208 |
| 4 | Cl | F | S | ![CF3 phenyl] | 176 |
| 5 | Cl | F | S | ![F-CF3 phenyl] | 139 |
| 6 | F | F | O | ![F-CF3 phenyl] | 182 |

It is understood that the specification and examples are illustrative but not limitative of the present invention and that other embodiments within the spirit and scope of the invention will suggest themselves to those skilled in the art.

We claim:

1. A benzoyl(thio)urea of the formula

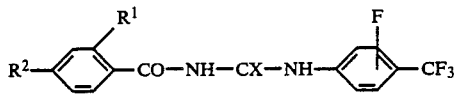

in which

X is oxygen or sulphur,

R¹ is halogen, and

R² is halogen.

2. A compound according to claim 1, in which

R¹ is fluorine, chlorine or bromine, and

R² is fluorine, chlorine or bromine.

3. A compound according to claim 1, in which

R¹ is fluorine or chlorine, and

R² is fluorine or chlorine.

4. A compound according to claim 1, wherein such compound is 1-(2-chloro-4-fluorobenzoyl)-3-(2-fluoro-4-trifluoromethyl-phenyl)-urea of the formula

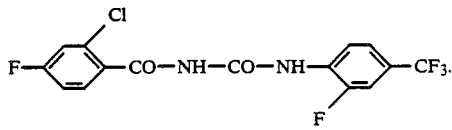

5. A compound according to claim 1, wherein such compound is 1-(2-chloro-4-fluorobenzoyl)-3-(3-fluoro-4-trifluoromethyl-phenyl)-urea of the formula

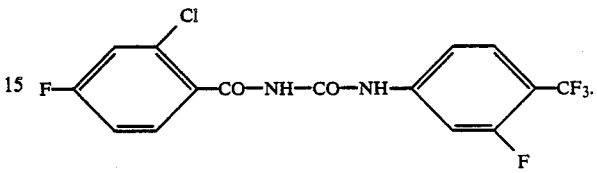

6. An arthropodicidal composition comprising an arthropodicidally effective amount of a compound according to claim 1 and a diluent.

7. A method of combating arthropods which comprises applying to such arthropods or to an arthropod habitat an arthropodicidally effective amount of a compound according to claim 1.

8. A method according to claim 7 wherein such compound is
1-(2-chloro-4-fluorobenzoyl)-3-(2-fluoro-4-trifluoromethyl-phenyl)-urea or
1-(2-chloro-4-fluorobenzoyl)-3-(3-fluoro-4-trifluoromethyl-phenyl)-urea.

* * * * *

UNITED STATES PATENT AND TRADEMARK OFFICE
CERTIFICATE OF CORRECTION

PATENT NO. : 4,782,091

DATED : Nov. 1, 1988

INVENTOR(S) : Sirrenberg et al.

It is certified that error appears in the above-identified patent and that said Letters Patent is hereby corrected as shown below:

Col. 9, line 60     Delete "100" and substitute --10--

Signed and Sealed this

Nineteenth Day of September, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,782,091

DATED : November 1, 1988

INVENTOR(S) : Wilhelm Sirrenberg et al

It is certified that error appears in the above-identified patent and that said Letters Patent is hereby corrected as shown below:

Title Page, No. "[75] Inventors:", line 4     Delete "Krehen" and substitute --Krehan--

Signed and Sealed this

Twelfth Day of December, 1989

Attest:

JEFFREY M. SAMUELS

*Attesting Officer*     *Acting Commissioner of Patents and Trademarks*